United States Patent [19]

Lebacq

[11] Patent Number: 5,139,812

[45] Date of Patent: Aug. 18, 1992

[54] METHOD AND APPARATUS FOR HIGH SECURITY CRYPTO-MARKING FOR PROTECTING VALUABLE OBJECTS

[75] Inventor: Philippe Lebacq, Paris, France

[73] Assignee: Bioprobe Systems, Paris, France

[21] Appl. No.: 545,607

[22] Filed: Jun. 29, 1990

[30] Foreign Application Priority Data

Jul. 7, 1989 [FR] France ................ 89 09202

[51] Int. Cl.$^5$ ................................ B41M 3/14
[52] U.S. Cl. ........................ 427/7; 118/31.5; 118/201; 118/211; 427/145; 427/338; 427/337
[58] Field of Search ............ 427/7, 145, 338, 337; 283/73, 74, 95, 98, 100; 118/31.5, 201

[56] References Cited

U.S. PATENT DOCUMENTS

1,689,302  10/1928  Smith .......................... 427/7

FOREIGN PATENT DOCUMENTS

| | | |
|---|---|---|
| 0090130 | 10/1983 | European Pat. Off. |
| 3742706 | 6/1989 | Fed. Rep. of Germany. |
| 232246 | 4/1925 | United Kingdom ............ 427/7 |
| 423046 | 1/1935 | United Kingdom ............ 427/7 |

*Primary Examiner*—Janyce Bell
*Attorney, Agent, or Firm*—Dennison, Meserole, Pollak & Scheiner

[57] ABSTRACT

A high security crypto-marking method for protecting valuable objects in which a target chemical compound suitable for subsequent detection by an appropriate detection means is applied to an object to be marked, wherein the method comprises the following operations:

a) preparing a solution of a target nucleic acid having a sequence selected to form a marking pattern and possessing a selected degree of fluidity;

b) incorporating a chosen quantity of the solution in each object of a class of objects to be marked;

thereby making it possible, subsequently, and should the occasion arise, to perform the following operation:

c) identifying or authenticating the object by using means for detecting the nucleic acid in order to reveal the marking.

The invention can be used, where required, to provide irrefutable proof of ownership of an object in the event of theft, resale, or forgery.

26 Claims, 2 Drawing Sheets

METHOD AND APPARATUS FOR HIGH SECURITY CRYPTO-MARKING FOR PROTECTING VALUABLE OBJECTS

The invention relates to marking valuable objects, in particular works of art or documents in order to protect them from theft, resale, or forging (in the sense of dishonest alteration or disguise).

The invention relates more particularly to a method and apparatus for crypto-marking suitable for marking valuable objects and making it possible subsequently, should the need arise, to identify or authenticate said objects in a manner which is irrefutable.

BACKGROUND OF THE INVENTION

The term "crypto-marking" is used in the present specification to designate marking which is concealed and invisible in a hidden location on the object, known only to its proprietor and undetectable by third parties.

The invention is particularly applicable to identifying works of art such as: paintings, sculptures, ceramics, pottery, vases, furniture, ancient clothes, carpets, tapestries, ancient books, engravings, etchings, collectors' items, etc.

The invention is also applicable to identifying modern durables such as cars, stereo systems, computers, televisions, radios, video recorders, cameras, etc.

The invention is also applicable to providing protection for all sorts of documents and official papers against forging, and in particular bank documents, checks, contracts, wills, paper money, identity documents, legal papers, etc.

At present there are very few means for protecting valuable objects such as works of art or other movable property against theft, resale, or forging. In addition, it is very difficult for an owner to be able to provide irrefutable proof of ownership of an item of stolen or resold property, once it has been found.

Another difficulty stems from the fact that not all works of art are listed. Although paintings by great masters may indeed be listed, the same does not apply to furniture, in particular.

According to folk wisdom: "possession is nine-tenths of the law". In France, this concept is laid down more formally in Article 2279 of the Civil Code which states:

"For movable property, possession gives title. Nevertheless, anyone who has lost a thing or an object, or from whom it has been stolen may, during a period of three years counted from the day of loss or theft, claim back that thing or object from any person in whose hands it is found; without prejudice to any remedy which that person may have against a third party from whom he obtained the thing or object."

Under these conditions, it is absolutely essential in the event of theft or loss to be able to prove ownership in goods, should the goods ever be found in the hands of a third party.

Presently existing means for protecting valuable objects, in particular works of art, include using metal implants which the owner of the object inserts in a special location on the object, known only to the owner.

Thus, in the event of loss or theft, if the object is found in the hands of a third party, the owner is theoretically in a position to prove ownership by taking out the implant or by causing the object to be X-rayed in the region containing the implant.

Unfortunately, a procedure of this type is not completely reliable since the implant may be detected by the third party, e.g. by using X-rays or gamma rays.

Proposals have also been made to apply a selective chemical compound or "target" compound on the object to be protected, which compound is suitable for subsequent detection by any appropriate means, in particular by means of another chemical compound or "probe" compound.

Thus, European patent application No. 0 090 130 proposes a method of authenticating a document by means of a color reaction system using a color-forming substance and a color-developing substance. One of the two substances is applied to the object, while the other substance is used for detection purposes. When the two substances are put into contact with each other, a characteristic color-reaction takes place, thereby enabling the document to be authenticated.

Given the limited number of color reaction systems suitable for this application, such a method is also lacking in reliability.

Consequently, an object of the invention is to provide a method capable of giving irrefutable proof of ownership of a valuable object, in particular of a work of art.

Another object of the invention is to provide a crypto-marking method capable of guaranteeing that a valuable object can be identified, with the marking itself being suitable for being delivered and performed by a valuer using the method of the invention.

Another object of the invention is to provide a method suitable for identifying official documents and papers such as contracts, deeds, wills, official papers, folding money, checks, share certificates, etc.

Another object of the invention is to provide such a crypto-marking method in which the marking of the valuable object cannot be detected by a third party, in particular by detection methods based on X-rays or on gamma rays.

Finally, another object of the invention is to provide a crypto-marking apparatus suitable for implementing the method of the invention.

The invention provides crypto-marking of valuable objects by taking advantage of the spectacular progress that has been made in biology over the last few years, making available molecular tools which are very highly effective. Of the various advances that have been made, the nucleic probe technique certainly constitutes the tool which is the most attractive and the most powerful.

The nucleic probe technique is based on the high degree of affinity which exists between two complementary strands of nucleic acid. This affinity is well illustrated by theoretical estimates of the dissociation constant Kd for a hybrid or "duplex" of 273 base pairs. This value is about $10^{-23}$M at 5° C. below the half denaturation temperature (Tm) of the duplex. By way of comparison, antigen-antibody actions have a Kd in the range $10^{-5}$M to $10^{-9}$M.

Using this technology, it is possible to construct nucleic probes (probe nucleic acids) of sequences that are complementary to the sequences of target nucleic acids and to perform duplex formation in vitro.

If the probe is labelled, radioactively or otherwise, the duplex formed in this way can be detected.

The use of nucleic probes thus makes it possible to detect living organisms (all of which normally carry nucleic acids representative of their genetic inheritance), providing the sequence or a portion of the sequence of the nucleic acids of said organisms is known.

The previously labelled probe is suitable for hybridizing with the target nucleic acid contained in the organism under consideration causes a hybrid or duplex to be obtained, and the labelling makes it detectable.

Numerous viruses, bacteria, parasites, fungi, etc. can thus be detected in biological media.

Nucleic probes also make it possible to perform genetic studies on more complex living organisms such as plants, animals, and human beings.

Such studies can be used, for example, to investigate and avoid genetic disorders, to identify the father or the mother in an affiliation action, to identify a rapist or a criminal amongst suspects, etc.

So far, nucleic probes have been used solely in medical, agro-food, or scientific applications for which nucleic acids and in particular nucleic probes constitute a powerful tool.

Surprisingly, the Applicant has observed that nucleic probe technology may also be used successfully in protecting valuable objects, in particular works of art, by providing absolutely irrefutable proof of the ownership of objects that have been stolen, resold, or forged, providing only that the objects were previously marked by the method of the invention.

SUMMARY OF THE INVENTION

More particularly, the present invention provides a high security crypto-marking method for protecting valuable objects in which a target chemical compound suitable for subsequent detection by an appropriate detection means is applied to an object to be marked.

According to the invention, the method comprises the following operations:

a) preparing a solution of a target nucleic acid having a sequence selected to form a marking pattern and possessing a selected degree of fluidity;

b) incorporating a chosen quantity of said solution in each object of a class of objects to be marked;

thereby making it possible, subsequently, and should the occasion arise, to perform the following operation:

c) identifying or authenticating the object by using means for detecting said nucleic acid in order to reveal the marking.

Thus, the invention consists in using nucleic acid fragments (called target nucleic acids) which are specified by their sequence, their size, and their nature, and which are suitable for being used as detection targets in valuable objects such as works of art, durable goods, official papers, contracts, etc. A target nucleic acid can easily be hidden for subsequent detection, thereby providing proof of the ownership or the authenticity of a valuable object. The detection may be direct or by hybridization.

It should also be observed that the use of nucleic acids is particularly advantageous in that they are of exceptional robustness and longevity.

It may be observed that a nucleic acid, e.g. DNA, is a particularly tough molecule, especially under dry conditions. This solidity and even longevity of DNA is well illustrated by an example. DNA has been taken from Egyptian mummies and cloned by genetic engineering techniques, so as to be amplified and finally sequenced in order to study certain genes taken from mummies that are more than 5,000 years old.

In accordance with the invention, the target nucleic acid is easily incorporated in the object to be protected. It may thus be hidden in a work of art, a piece of furniture, a car, or any other article, or it may be incorporated in a paper, a contract, or an official document.

In a preferred implementation of the invention, operation b) consists in applying a solution of nucleic acid on a surface of a medium in order to impregnate it with said solution, and subsequently in incorporating the medium impregnated in this way in each object that is to be marked.

A medium may be made, for example, of nitrocellulose, polyamide (nylon) which is positively charged or not charged, paper, card, wood, plastic material, cloth, metal, glass, ceramics, earthenware, organic material in the form of beads or jelly, or even inorganic material.

A preferred medium comprises a small membrane suitable for being inserted either flat in a thin object or rolled up in a thicker object.

Advantageously, the target nucleic acid is applied to a medium made of nitrocellulose or of nylon which may optionally be positively charged, and which is small in size. For example, the membrane may be 5 mm wide by 15 mm long. Once it has been impregnated with the target nucleic acid, the medium may be rolled up, or folded, and glued or incorporated in the item to be marked.

In a variant, operation b) consists in applying the solution of nucleic acid directly on a surface of the object to be marked, in the event that the substance from which said surface is made enables said nucleic acid to adhere directly thereto.

Advantageously, during operation b), the nucleic acid solution is applied in the form of a mark by writing a number, a letter, a word, a phrase, a signature, or any other type of marking.

In a preferred implementation of the invention, during operation c), use is made of a detection means comprising a single strand nucleic acid probe whose sequence is complementary to that of the target nucleic acid incorporated in the object, which probe is capable of hybridizing therewith, thereby enabling the target nucleic acid to be specifically detected by molecular hybridization.

The target nucleic acid and the probe nucleic acid may be of different lengths, may have different sequences, and may be of different natures. It may be constituted by DNA or RNA of natural or synthetic origin, or by synthetic derivatives totally or partially constituted by rare bases or by modified bases.

The target nucleic acid sequence may be constituted by a sequence in the genome of a human being, or the entire genome of a human being, e.g. the owner of the object to be marked. Thereafter, the owner may be identified by nucleic hybridization in the same manner as is used for affiliation testing (DNA fingerprinting) by using "satellite" or repeated probes or any other type of probe suitable for generating polymorphism identifying the owner absolutely.

More generally, the invention may make use of any target nucleic acid capable of generating polymorphism suitable for being detected by satellite probes, repeated probes, etc. and any probe capable of detecting polymorphism.

In a preferred implementation of the invention, the target nucleic acid and the probe nucleic acid are complementary oligonucleotides whose sequences are obtained randomly, e.g. by means of a computer program.

Thus, the target nucleic acid is an oligonucleotide which is synthesized chemically. The sequence of the target nucleic acid is quite random and may be generated by means of a computer program or by any other means.

For example, if an oligonucleotide is used which is 50 nucleotides long, then the probability of finding the same sequence independently in nature or of synthesizing it randomly in the laboratory is one chance in $1.26 \times 10^{30}$, which constitutes an event which is highly unlikely. By way of example, it may be recalled here that the size of the entire haploid human genome is about $3 \times 10^9$ base pairs.

In this preferred implementation of the invention, the complementary sequence, i.e. the sequence of the probe nucleic acid, is likewise synthesized and is used as a probe.

If the probe nucleic acid finds a target nucleic acid of complementary sequence, then hybridization takes place forming a hybrid or duplex.

This hybrid may be detected by any appropriate detection means known in the field of nucleic probes.

Thus, the hybrid formed in this way may be detected after the probe has been labelled, or otherwise.

The probe may be labelled radioactively or otherwise by any appropriate labelling system known in the field of nucleic probes. To do this, use may be made, for example, of the labelling methods described in the following publications:

Langer P. R., Waldrop A. A., and Ward D. C. (1981) Proc. Natl. Acad. Sci. USA 78. 6633–6637.

Leary J. I., Brigati D. J., and Ward D. C. (1983) Proc. Natl. Acad. Sci. USA 80, 4045–4049.

Tchen P., Fuchs R. P. P., Sage E., and Leng M (1983) Proc. Natl. Acad. Sci. USA 81, 3466–3470.

Kenz M. (1983) EMBO J. 2, 817–822.

Kenz M., and Kurz C. (1983) Nucleic Acids Res. 12, 3435–3444.

Jablonski E., Moomaw E. W., Tullis R. II., and Ruth J. L. (1986) Nucleic Acids Res. 14, 6115–6128.

Traincard F., Ternyck T., Dauchin A., and Avramaes S. (1983) Ann, Immunol. (Inst. Pasteur) 134 D. 399–405.

When the probe is not labelled, the hybrid may be detected specifically or non-specifically by means of antibodies which detect single or double strand nucleic acids, or proteins, or compounds having an affinity for nucleic acids.

For example, detection may be performed by means of antihybrid antibodies. These are antibodies bonded to a detection enzyme and which are incapable of fixing onto a single strand nucleic acid but which, in contrast, are capable of fixing onto a double strand nucleic acid, such as a hybrid.

Consequently, if a hybrid is formed, the antihybrid antibody fixes onto the hybrid and this can be shown up by the detection enzyme.

The hybrid can be detected not only by chemical means, but also by physical means, e.g. electrical means, electronic means, radio means, or magnetic means.

It is possible, in particular, to use a piezoelectric detection system which emits a special signal when hybridization takes place. This signal may be detected and amplified by any suitable electronic system.

In a preferred implementation of the invention, the probe is labelled by a non-radioactive labelling method. Advantageously, the labelling and label development are nonradioactive using labelling based on biotine, on sulfonation, or on the labelling method described in French patent application No. 88 09598 and certificate of addition application No. 89 03192 filed by the present Applicant.

The target nucleic acid is preferably spread over the medium or directly over the object if possible, using an appropriate applicator means.

The applicator means may be a pen (a pen having a nib, a ballpoint, or a felt tip), a drawing instrument, a paintbrush, or an automatic machine such as an ink jet machine.

In a preferred implementation of the invention, the application is performed by means of a pen having a cartridge containing a solution of the probe nucleic acid in a suitable buffer providing good fluidity and good conservation of the nucleic acid. The concentration is determined in such a manner as to make it easy subsequently to develop the target nucleic acid and also to make it easy to write with the pen.

By way of example, the concentration may be such that the applicator means deposit 10 picograms (pg) to 10 nanograms (ng) of nucleic acid per $mm^2$. Preferably, a quantity of 1 $ng/mm^2$ appears to be advantageous. By way of example, the following buffer may be used:

Tris 50 mM pH=8
EDTA 20 mM
Tween 20 0.3%
NaCl 25 mM
Sodium azide 0.4% (or any other preservative).

In a preferred implementation of the invention, a 5-digit number is written using the nucleic acid solution and the pen, on the medium or else directly on the object itself. Once it has dried, the number is quite invisible and can only be developed or revealed by means of a probe nucleic acid having a sequence complementary to that of the target nucleic acid, which sequence is known only to the owner of the object.

For developing the number, hybridization conditions are important, particularly with oligonucleotides. Hybridization kinematics depend on the concentration of sodium ions in the medium, on the nature of the medium, and on the hybridization temperature. This temperature itself depends on the stability of the hybrids to be formed. Finally, the stability is directly related to the guanine and cytosiné (GC) base content of the nucleic acid.

Given the random nucleotide sequence obtained for constituting the target nucleic acid, it is possible to calculate the cytosine and guanine base percentage of the oligonucleotide and thus to define optimum hybridization conditions.

Development should be performed under these conditions and these conditions only.

In another variant of the invention, detection means may be used which are non-specific for the target nucleic acid. In other words, such means are capable of recognizing, nonspecifically, a target nucleic acid sequence.

Naturally, in order to provide irrefutable proof of ownership of a marked object, in accordance with the method of the invention, it is most particularly desirable to use specific detection means, as described above.

In another aspect, the present invention provides apparatus for high security crypto-marking to protect objects of value, the apparatus including a target chemical compound suitable for subsequent detection by appropriate detection means.

According to the invention, the apparatus comprises:

a solution of a target nucleic acid having a selected sequence constituting a marking pattern and possessing a selected degree of fluidity;

applicator means suitable for spreading said solution on a surface to be marked; and nucleic acid detection means.

Advantageously, said solution also contains a buffer suitable for conserving the target nucleic acid and for conferring a sufficient degree of fluidity to said solution to enable it to be used in the applicator means.

For example, this applicator means may be a pen, a paintbrush, a drawing instrument, or an automated machine, as mentioned above.

Advantageously, the apparatus of the invention further includes a medium constituting a surface to be marked by the solution and suitable for being incorporated in an object to be marked.

The medium is constituted by a substance selected from those specified above.

The medium may be incorporated in a sheet of a document, e.g. in a window or at the bottom of a page, by stamping and/or sticking using a security hologram strip.

Various different types of document may be made in this way, in particular pages of a contract suitable for receiving the signatures of the contracting parties on one or more media disposed in appropriate manner. If attempts are made to falsify the document by replacing one medium by another, the hologram strip is deformed and it can immediately seen whether fraud has been attempted. The hologram strip is advantageously a thin aluminum strip which has been subjected to appropriate holographic treatment.

BRIEF DESCRIPTION OF THE DRAWINGS

An embodiment of the invention is described by way of example with reference to the accompanying drawings, in which.

DETAILED DESCRIPTION

Figures 1, 2:
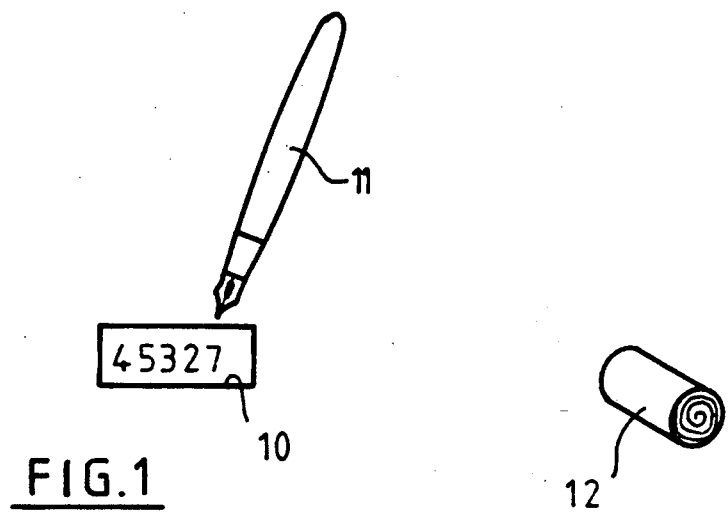
FIG. 1 shows a medium suitable for being marked using the method of the invention by means of an applicator pen.
FIG. 2 shows the same medium after it has been rolled up.

Reference is made initially to FIG. 1 which shows a medium 10 of the invention constituted, in the present example, by a rectangular membrane of 5 mm by 15 mm, giving an area of about 75 mm². This medium is advantageously constituted by a polyamide (nylon) membrane or by a nitrocellulose membrane.

For example, it is possible to use membranes such as those sold under the trademark Zeta-Probe or under the trademark Zeta-Bind by the American firm CUNO. It is also possible to use nylon membranes such as those sold under the trademarks Gene-Screen Normal and Gene-Screen Plus by the U.S. firm Dupont de Nemours.

It is also possible to use a nylon membrane such as that sold under the trademark Hy-Bond by the British firm Amersham.

It is also possible to use a nitrocellulose membrane as sold by the West German firm Schleicher & Schuell.

The membrane 10 of FIG. 1 receives a solution of target nucleic acid prepared as described above and applied by means of a pen 11. In the example shown, a 5-digit number known only to the owner of the object is written on the membrane. After the solution has dried, the number applied on the medium in this way is quite invisible.

Thereafter, in the example shown, the membrane 10 is rolled up to form a roll 12, as shown in FIG. 2, which roll occupies a very small volume since the area of the medium when flat is about 75 mm² and the thickness of the membrane is a few tenths of a millimeter. Once the membrane has been rolled up in this way, the volume occupied by the roll 12 is a few mm³. The roll 12 made in this way can be hidden in the object to be protected at a location known only to its owner.

Figure 3:
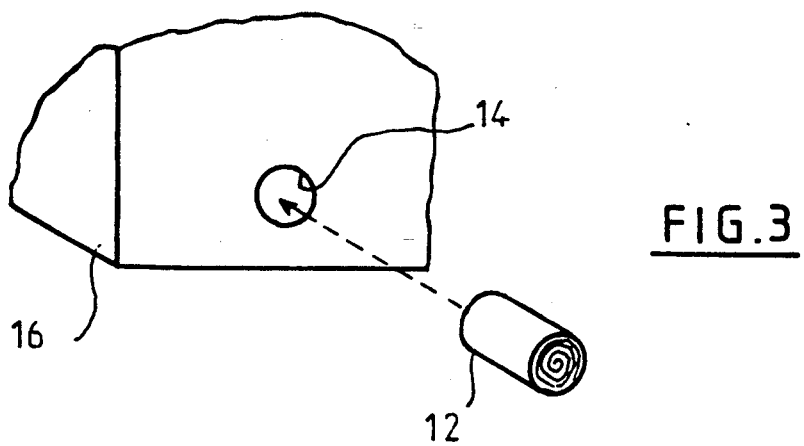
FIG. 3 shows the rolled up medium prior to being inserted in an appropriate housing formed inside the object to be protected.

As shown in FIG. 3, a hole 14 may be drilled by means of a minidrill in a region of the object 16 to be protected and the roll 12 can then be inserted in the hole formed in this way. Thereafter, the hole can be plugged by means of an appropriate plugging compound so as to leave no visible trace of the hole itself.

Figure 4:
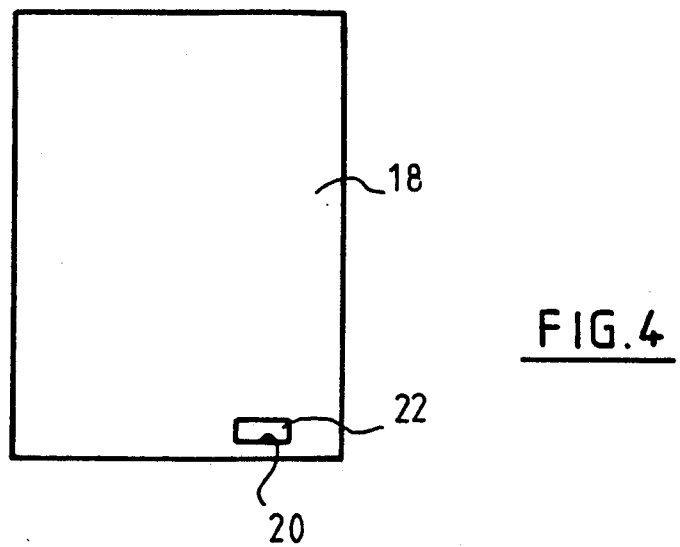
FIG. 4 shows a document incorporating a medium of the invention.

Reference is now made to FIG. 4 which shows a document 18, e.g. a sheet of letter paper, which is generally rectangular in shape and which includes a rectangular window 20 near the bottom thereof. A membrane 22 made of nitrocellulose or of nylon which may be positively charged or not is inserted in the window 20. It is thus possible to write, sign, or make any other kind of recognition symbol on the membrane 22. Here again, such symbols, letters, words, phases, or signatures are quite invisible after drying.

Figure 5:
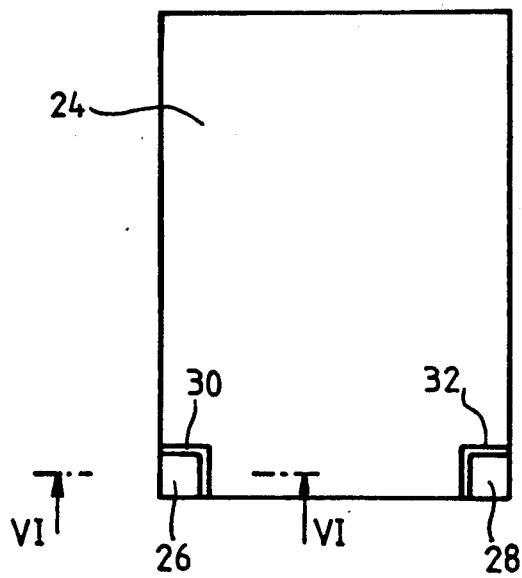
FIG. 5 shows a document incorporating two media of the invention.
Figure 6:
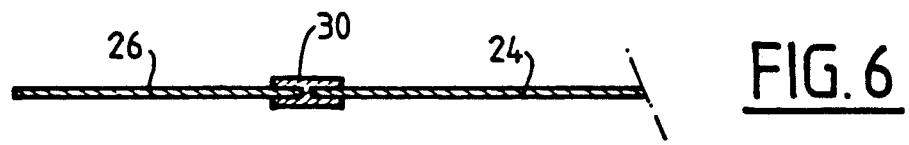
FIG. 6 is a cross-section on a larger scale on line VI—VI of FIG. 5.

Reference is now made to FIG. 5 which shows a document 24, e.g. a sheet of letter paper or a sheet of contract which includes two membranes 26 and 28 at the bottom thereof, the membranes being made of nitrocellulose or of nylon and constituting media of the invention. These two membranes are square having a side of a few millimeters in length and they are disposed in the bottom corners of the document which are cut off for this purpose. Each of the membranes is fixed to the document by a hologram strip 30, 32 as shown more clearly in FIG. 6. Each of the hologram strips is advantageously a sheet of aluminum foil which has been holographically treated and which is stamped and/or glued in order to fix it to the membrane. Each strip comprises two portions applied respectively to the front and to the back of the document.

Figure 7:
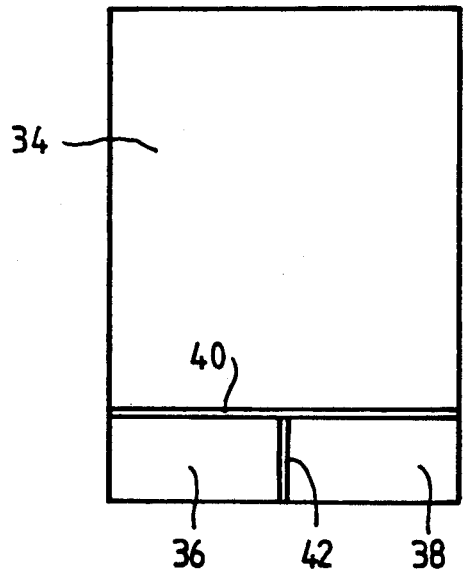
FIG. 7 shows a document incorporating two media of the invention, in accordance with a variant embodiment.

In the embodiment of FIG. 7, the document 34 is provided at the bottom of the page with two rectangular membranes 36 and 38, and together they extend over the entire width of the document. The two membranes are connected to the document 34 by a hologram strip 40 which extends across the entire width of the document, and they are connected to each other by a hologram strip 42 which may be a few cm long.

The membranes 26, 28, 36, and 38 may be used for receiving the signatures of the contracting parties.

The target nucleic acid applied in this way to the membrane 10 of FIG. 1, to the membrane 22 of FIG. 4, to the membranes 26 and 28 of FIG. 5, or to the membranes 36 and 38 of FIG. 7 can only be developed or "revealed" by means of a complementary probe suitable for identifying or authenticating either the object 16 of FIG. 3, or the documents 18, 24, and 34 of FIGS. 4, 5, and 7. The document may be a deed, a contract, folding money, a check, a share certificate, a will, etc.

The invention thus provides the owner of an object to be marked by the method of the invention with three safeguards.

Firstly, the medium (e.g. a nylon membrane) may be hidden in a location known only to the owner. The hidden membrane is not detectable by means of X-rays since both the membrane and nucleic acid are completely transparent to X-rays and to gamma rays. Further, the volume occupied by the membrane is extremely small since when rolled up it occupies only a few mm$^3$.

Secondly, only the owner of the object knows the number written on the medium.

Thirdly, the hybrid can be developed or "revealed" only by using a probe constituted by a complementary nucleic sequence, known only to the owner, and this can take place only under hybridizing conditions defined by the cytosine and guanine base content of the hybrid. However, this content is determined on the basis of the target nucleic sequence which is known only to the owner of the object to be protected.

The mark may be developed or "revealed" in the presence of a bailiff or other witness under oath guaranteeing that the detection operation takes place normally using the special complementary probe held by the owner of the object to be protected.

When the object to be protected is a paper or a document, it is easy to include fragments of medium, e.g. nylon membrane, and to write any numeric code, signature, or other recognizable symbol thereon enabling the document to be identified.

The paper from which the document is made may be ordinary paper or special paper, e.g. a fluorescent security paper.

Such papers exist containing fluorescent patterns such that when irradiated in ultraviolet light, they emit light radiation of various different colors.

I claim:

1. A high security crypto-marking method for protecting valuable objects in which a target chemical compound suitable for subsequent detection by an appropriate detection means is applied to an object to be marked, wherein the method comprises the following operations:
   a) preparing a solution of a target nucleic acid having a known nucleotide sequence and possessing a selected degree of fluidity;
   b) incorporating a chosen quantity of said solution in each object of a class of objects to be marked; and
   c) identifying or authenticating the object by bringing a probe means including a chemical agent reactive with said target nucleic acid into contact with said target nucleic acid, and detecting a reaction between said agent and said target nucleic acid and/or a reaction product.

2. A method according to claim 1, wherein operation b) comprises applying a solution of nucleic acid on a surface of a medium in order to impregnate it with said solution, and subsequently in incorporating the medium impregnated in this way in each object that is to be marked.

3. A method according to claim 2, wherein the medium is made of a substance selected from the group consisting of nitrocellulose, nylon, nylon which is positively charged, paper, card, wood, plastic material, cloth, an organic substance in the form of beads or of a gel, and an inorganic substance.

4. A method according to claim 2, wherein the support is a membrane of small size suitable for being inserted flat in a thin object or suitable for being rolled up to form a roll suitable for insertion in a thick object.

5. A method according to claim 1, wherein operation b) comprises applying the solution of nucleic acid directly on a surface of the object to be marked, wherein the substance from which said surface is made enables said nucleic acid to adhere directly thereto.

6. A method according to claim 1, wherein during the operation b), the nucleic acid solution is applied in the form of a mark by writing at least one element selected from the group consisting of a number, a letter, a word, a phase, and a signature.

7. A method according to claim 1, wherein said chemical agent comprises a single strand nucleic acid whose sequence is complementary to that of the target nucleic acid incorporated in the object, which single strand nucleic acid is capable of forming a hybrid with the target nucleic acid, thereby enabling the target nucleic acid to be specifically detected by molecular hybridization.

8. A method according to claim 7, wherein the hybrid is detected by a method selected from the group consisting of radioactive compounds, non-radioactive compounds, direct detection means, indirect detection means, chemical means, and physical means.

9. A method according to claim 1, wherein the target nucleic acid and the chemical agent are selected from the group consisting of DNA and RNA of natural and of synthetic origin, from synthesized derivatives containing at least in part at least one of rare bases and modified bases, from nucleic sequences and genomes suitable for generating polymorphism, and from genome sequences and entire genomes of human beings.

10. A method according to claim 9, wherein the target nucleic acid and the chemical agent are complementary oligonucleotides whose sequences are obtained randomly.

11. A method according to claim 7, comprising determining base contents of cytosine and quanine for a randomly generated target nucleic acid and performing hybridization under specific conditions depending on the cytosine and guanine base content of the target nucleic acid sequence as randomly generated.

12. A method according to claim 1, wherein the target nucleic acid solution contains a buffer suitable for conserving the nucleic acid and for ensuring that the solution is sufficiently fluid to enable it to be applied, and wherein applicator means are used for spreading said solution and forming symbols on a surface to be marked.

13. A method according to claim 1, wherein said chemical agent is non-specific for said target nucleic acid.

14. A kit for high security crypto-marking for protecting valuable objects, said kit comprising:
   a solution of a target nucleic acid having a known nucleotide sequence and possessing a selected degree of fluidity;
   applicator means suitable for spreading said solution on a surface to be marked; and probe means comprising a chemical agent reactive with said target nucleic acid and means for detecting a reaction between the target nucleic acid and chemical agent and/or a reaction product, wherein said solution contains a buffer for conserving the target nucleic acid and for conferring to the solution a degree of fluidity sufficient for use in said applicator means.

15. Kit according to claim 14, wherein the concentration of target nucleic acid in the solution is such that the applicator means deposits 10 pg to 10 ng of nucleic acid per mm$^2$ of surface to be marked.

16. Kit according to claim 14, wherein the applicator means is constituted by an implement selected from the group a ballpoint pen, a nib pen, a felt tip pen, a paintbrush, a drawing instrument, and an automated machine.

17. Kit according to claim 14, further including a medium constituting a surface to be marked by the solution and suitable for being incorporated in the object to be marked.

18. Kit according to claim 17, wherein the medium is made of a substance selected from the group consisting of nitrocellulose; nylon nylon which is positively charged; paper; card; wood; plastic material; cloth; an organic substance in the form of a bead or a gel; and an inorganic substance.

19. Kit according to claim 17, wherein the medium is incorporated in a sheet of a document by a means selected from the group consisting of a stamp and a hologram strip.

20. Kit according to claim 14, wherein the chemical agent is specific to the target nucleic acid.

21. Kit according to claim 14, wherein the chemical agent is non-specific for the target nucleic acid.

22. A method according to claim 3, wherein said inorganic substance is metal, glass, ceramics, or earthenware.

23. A method according to claim 8, wherein said physical means is electrical means, electronic means, radio means or magnetic means.

24. A method according to claim 10, wherein said sequences are obtained randomly by means of a computer program.

25. Kit according to claim 16, wherein said automated machine is an ink jet machine.

26. Kit according to claim 18, wherein said inorganic substance is metal, glass, ceramics, or earthenware.

* * * * *